United States Patent [19]

Bergstein et al.

[11] Patent Number: 5,431,900
[45] Date of Patent: Jul. 11, 1995

[54] ESTER-SUBSTITUTED DIAMINEDITHIOLS AND RADIOLABELED COMPLEXES THEREOF

[75] Inventors: Paul L. Bergstein, Norwood; Edward H. Cheesman, Townsend; Alan D. Watson, Andover, all of Mass.

[73] Assignee: The Du Pont Merck Pharmaceutical Company, Wilmington, Del.

[21] Appl. No.: 139,894

[22] Filed: Oct. 20, 1993

Related U.S. Application Data

[60] Division of Ser. No. 143,561, Jan. 26, 1988, Pat. No. 5,279,811, which is a continuation-in-part of Ser. No. 16,982, Feb. 18, 1987, abandoned.

[51] Int. Cl.[6] .................. A61K 51/04; C07C 321/00; C07F 13/00
[52] U.S. Cl. ........................ 424/165; 560/9; 560/18; 534/14
[58] Field of Search .................. 560/9, 18, 147, 153, 560/154; 424/1.65; 534/10, 14

[56] References Cited

U.S. PATENT DOCUMENTS

| | | | |
|---|---|---|---|
| 2,810,753 | 10/1957 | Bersworth | 260/534 |
| 4,284,619 | 8/1981 | Lin | 424/1.85 |
| 4,434,151 | 2/1984 | Byrne et al. | 424/1.65 |
| 4,444,690 | 4/1984 | Fritzberg | 534/14 |
| 4,571,430 | 2/1986 | Byrne et al. | 560/148 |
| 4,575,556 | 3/1986 | Byrne et al. | 549/63 |
| 4,615,876 | 10/1986 | Troutner et al. | 534/14 |
| 4,638,051 | 1/1987 | Burns et al. | 534/14 |
| 4,673,562 | 6/1987 | Davison et al. | 424/1.65 |
| 4,746,505 | 5/1988 | Jones et al. | 424/1.65 |
| 4,897,255 | 1/1990 | Fritzberg et al. | 530/391.5 |
| 4,963,688 | 10/1990 | Bodor | 424/1.1 X |
| 5,037,631 | 8/1991 | Nosco | 424/1.65 |
| 5,175,343 | 12/1992 | Fritzberg et al. | 560/145 |
| 5,279,811 | 1/1994 | Bergstein et al. | 424/1.65 |

FOREIGN PATENT DOCUMENTS

| | | | |
|---|---|---|---|
| 0123504 | 4/1984 | European Pat. Off. | A61K 49/02 |
| 0135160 | 8/1984 | European Pat. Off. | A61K 49/02 |
| 0163119 | 4/1985 | European Pat. Off. | |
| 0200211 | 4/1986 | European Pat. Off. | |
| 0232751 | 1/1987 | European Pat. Off. | |
| 742996 | 1/1953 | United Kingdom | |

OTHER PUBLICATIONS

European Search Report-EP 88102252.9.
J. Nucl. Med., 23 (9), 801–809 (1982).
J. Nucl. Med., 23 (7) 592–598 (1982).
J. Nucl. Med., 22 (3), 258–263 (1981).
J. Nucl. Med., 24 (4), 353–355 (1983).
Inorganic Chem., 20 (6), 1629–32 (1981).
Radiopharmaceutical Chem., Abstracts, 333 (Aug. 1982).
J. Nucl. Med., 23 (5), 17 (1982).
J. Nucl. Med., 22 (6), pp. 38, 51, 52 (1981).
J. Nucl. Med., 24 (5), 80 (1983).
J. Nucl. Med., 20 (6), 653 (1979).
J. Nucl. Med., 22 (6), 57–58, 641 (1979).
Can J. Chem., 45, 49 (1967).
J. Am. Chem. Soc., 108, 1351 (1986).
Fritzberg, A. R. "Advances in Tc–Labeling of Antibodies", Nucl. Med. 1987, 26. 7–12.

*Primary Examiner*—Sean M. Wu
*Attorney, Agent, or Firm*—Gerald J. Boudreaux

[57] ABSTRACT

Radiopharmaceuticals consisting essentially of a lipophilic, charge neutral radionuclide complex of a diaminedithiol ligand having 1–4 ester groups of the formula —A—COOR where A is a straight or branched chain alkylene of 0–10 carbon atoms and R is an alkyl group of 1–10 carbon atoms are useful in radioimaging brain perfusion in primates. Ester-substituted diaminedithiols in sterile, pharmaceutically acceptable form, and kits of the diaminedithiols and sterile, non-pyrogenic reducing agents for reducing preselected radionuclides are also provided. Technetium-99m is a preferred radionuclide.

25 Claims, No Drawings

ESTER-SUBSTITUTED DIAMINEDITHIOLS AND RADIOLABELED COMPLEXES THEREOF

CROSS REFERENCE TO RELATED APPLICATIONS

This application is a divisional of Ser. No. 07/143,561, filed Jan. 26, 1988 now U.S. Pat. No. 5,279,811, which is a continuation-in-part of Ser. No. 07/016,982, filed Feb. 18, 1987 now abandoned.

FIELD OF THE INVENTION

This invention relates to radionuclide complexes of ester-substituted diaminedithiols as radiopharmaceuticals, processes for their kits for the preparation and delivery of the radiopharmaceuticals to target organs for imaging in primates, and methods of using them as diagnostic agents.

BACKGROUND OF THE INVENTION

Radiopharmaceutical compounds have been in use for diagnostic purposes for many years and one skilled in the art of nuclear medicine and radiopharmaceutical research is well aware of the for a diagnostically useful radiopharmaceutical. Briefly, these requirements include: efficient preparation of the radiopharmaceutical, such that preparation in the hospital or pharmacy is possible; efficient transport of the radiopharmaceutical to the target organ; efficient extraction of the radiopharmaceutical by the target organ, such that adequate target to background ratios are achieved to allow diagnostic distinctions; adequate retention in the target organ to allow detection using conventionally available radiation monitoring equipment Diaminedithiol complexes of technetium-99m as radiopharmaceuticals have been described previously. Both Burns et al. in European Patent Application 163,119, published Dec. 4, 1985, and Kung et al. in European Patent Application 200,211, published Nov. 5, 1986, describe the use of amine derivatized diaminedithiol complexes of technetium-99m as radiopharmaceuticals useful for determining regional cerebral blood flow. While these complexes have been shown to exhibit adequate uptake into the brains of mammals to provide good target to background ratios, these compounds have shown rather rapid washout from the brain tissue, restricting their usefulness for single photon emission computed tomography with conventionally available equipment.

Lin, U.S. Pat. No. 4,284,619 issued August 18, 1981 describes the use of esters as brain imaging agents. Specifically described are esters of iodinated benzoic acids. These compounds showed very poor brain retention, with the brain to blood ratio at 5 minutes being less than 0.5 in all cases.

Davison et al. in European Patent Appln. No. 135,160, published Mar. 27, 1985, describe the use of a variety of substituted diamidedithiol complexes of technetium-99m as renal imaging agents. These diamidedithiol ligands result in the formation of anionic complexes with technetium, resulting in high renal extraction, but the anionic charge on these complexes appears to eliminate the potential for adequate brain extraction. Similar anionic complexes are described by Fritzberg, U.S. Pat. No. 4,444,690 issued Apr. 24, 1984; and by Byrne et al., U.S. Pat. No. 4,434,151 issued Feb. 28, 1984; U.S. Pat. No. 4,571,430 issued Feb. 18, 1986; and U.S. Pat. No. 4,575,556 issued Mar. 11, 1986.

Troutner et al. in European Patent Appln. No. 123,504, published Oct. 31, 1984, describe neutral technetium-99m complexes with alkylene amine oximes and their use as radiopharmaceuticals for the evaluation of regional cerebral blood flow. While these compounds have shown adequate brain extraction as well as prolonged retention in the brain of mammals, these complexes convert on standing to a hydrophilic complex which is no longer effective as a radiopharmaceutical for evaluation of regional cerebral blood flow. This conversion with time requires that the radiopharmaceutical be used within 30 minutes after preparation.

Clearly the need exists for more effective radiopharmaceuticals for the evaluation of regional cerebral blood flow which will combine the necessary properties of adequate brain uptake, adequate retention within the brain, distribution in accordance to blood flow, and adequate stability after preparation to be useful in the clinical environment.

U.S. Pat. No. 2,810,753 issued Oct. 22, 1957, describes di-sulfhydryl alkylene diamine polycarboxylic acids as metal ion chelating agent. Some of these acids are immediate precursors to the ester-substituted diaminedithiols of the present invention.

Blondeau et al., Can. J. Chem., 45, 49 (1967), describe the reductive dimerization of thiazolidines to yield N,N'-1,2-ethylenediylbis-L-cysteine derivatives.

A copper complex of N,N'-1,2-ethylenediylbis-L-cysteine. dimethyl ester prepared from the dimethylester dihydrochloride is characterized by Bharadwaj et al., J. Am. Chem. Soc., 108, 1351 (1986).

SUMMARY OF THE INVENTION

According to the present invention there is provided an ester-substituted diaminedithiol of the formula:

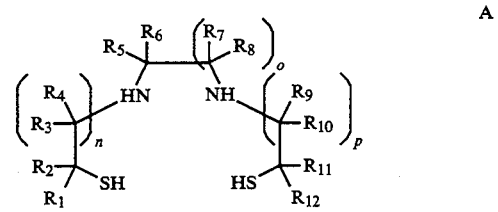

A

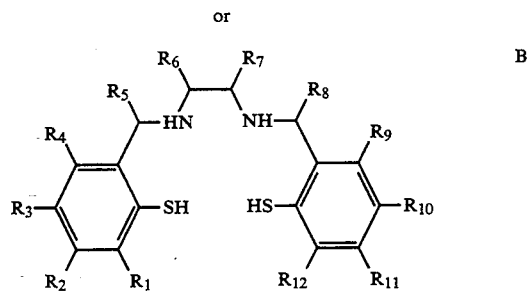

B or a pharmaceutically suitable salt thereof wherein:
each of $R_1$–$R_{12}$ individually is selected from the group consisting of H, alkyl of 1–10 carbon atoms and —A—COOR wherein A is a straight or branched chain alkylene of 0–10 carbon atoms, n, o, and p are independently 1 or 2, and R is (a) alkyl of 1–10 carbon atoms, (b) phenyl or benzyl optionally substituted with up to 5 ring substituents each selected from alkyl of 1–4 carbon atoms, fluoro, chloro, bromo, nitro, alkoxy of 1–4 carbon atoms, carboxyl, or a carboxylic acid ester of 1–4 carbon atoms, or (c) a 5- or 6-membered heterocyclic ring containing 1 or 2 heteroatoms selected from N, O or S, with the proviso that at least one of $R_1$–$R_{12}$ is —A—COOR, said ester-substituted diaminedithiol in sterile, pharmaceutically acceptable form.

Also provided is a kit which comprises a predetermined quantity of a sterile, pharmaceutically acceptable ester-substituted diaminedithiol as described above and a predetermined quantity of a sterile, non-pyrogenic reducing agent for reducing a preselected radionuclide.

Further provided is a radiopharmaceutical consisting essentially of a lipophilic, charge neutral radionuclide complex of a diaminedithiol ligand having at least 1 ester group of the formula —A—COOR where A and R are as defined previously.

Additionally provided is a process of radioimaging comprising administering parenterally to a mammal a radiopharmaceutical as set forth above in a pharmaceutically suitable carrier and radioimaging the brain of the mammal after allowing sufficient time for the composition to localize in the brain.

PREFERRED EMBODIMENTS

For the purposes of this invention, "lipophilic" will be understood to mean a radiopharmaceutical which readily crosses the blood brain barrier intact, i.e., a complex with an overall 1-octanol/saline partition coefficient in the range of 0.5 to 500, preferably 10 to 300, most preferably 10 to 100, as determined by mixing the complex with 1-octanol and saline (0.9% by weight in water) and measuring the proportion of the complex which partitions into each layer.

For the purposes of this invention, a "diaminedithiol" will be understood to be an organic ligand, which utilizes two amines and two thiols to coordinate with a radioactive metal, which may be unsubstituted or substituted on any or all of the carbon atoms. Preferred diaminedithiols include 1,10-dithia-4,7-diazadecanes, 1,12-dithia-5,8-diazadodecanes, 1,11-dithia-4,7-diazaundecanes, and 1,11-dithia-4,8-diazaundecanes.

It is preferred that the diaminedithiol be non-aminated. "Non-aminated" will be understood to mean that there are no additional amine substituents on any of the carbon atoms of the diaminedithiol.

The radionuclide used to form the radiopharmaceutical is selected from the radioactive isotopes of Tc, Ru, Cu, Co, Pt, Fe, Os, Ir, W, Re, Cr, Mo, Mn, Ni, Rh, Pd, Nb, and Ta, preferably, technetium-99m. When the radionuclide is technetium-99m in the form of the $Tc^VO$ core, it is readily apparent that one of the amines of the diaminedithiol must be deprotonated in the radiopharmaceutical complex to result in a complex which is charge neutral.

These preferred complexes can then be represented by the general formulas (Ia) and (Ib), but for the sake of clarity, only one of the two possible structures will be shown throughout the remainder of the specification, with the understanding that the two are equivalent. In addition to the $Tc^VO$ core, complexes can be formed which incorporate the TcN core, and in which both amines of the diaminedithiol complex remain protonated. Thus, when the radionuclide is technetium-99m, the complexes which are obtained are of the general formulas (I) and (II):

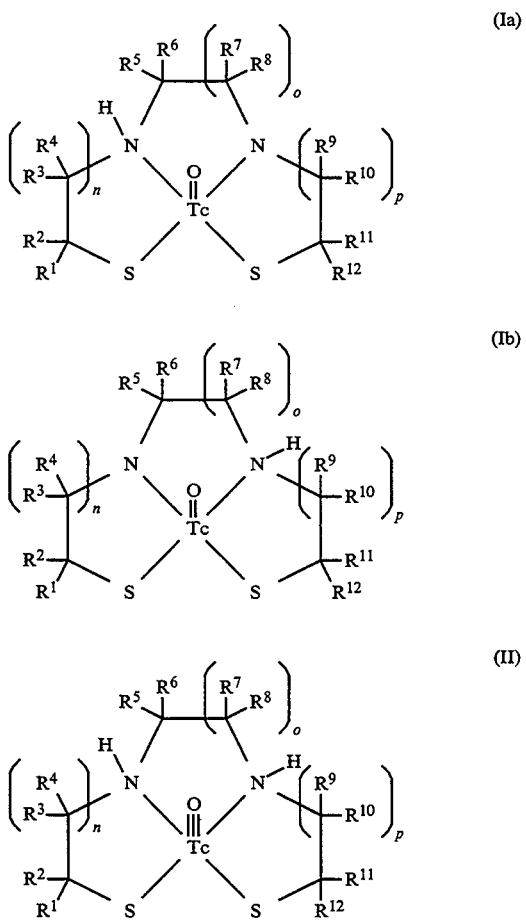

wherein each of $R^1$ to $R^{12}$ individually is selected from the group consisting of H, alkyl of 1–6 carbon atoms and —A—COOR where A is a straight or branched chain alkylene of 0–6 carbon atoms, n, o, p are each independently 1 or 2, and R is alkyl of 1–6 carbon atoms, with the proviso that at least one, but preferably no more than 4, of $R^1$–$R^{12}$ is —A—COOR.

Particularly preferred radiopharmaceuticals are prepared from diaminedithiols where:

a) n, o and p are 1; or b) each alkyl of R and $R_1$–$R_{12}$ is from 1–3 carbon atoms: or c) A is a straight chain alkylene of 0–3 carbon atoms, or d) $R^3$ $R^{10}$ and are —A—COOR and $R^4$ and $R^9$ are H; or e) A is a bond, i.e., O and R is ethyl; or f) A is a bond and stereochemistry at the position where that bond is attached to the diaminedithiol backbone is L(or R-).

Other technetium radiopharmaceuticals within the present invention have the general formulas:

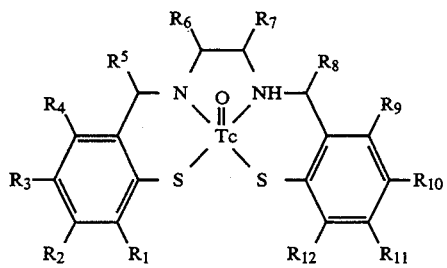

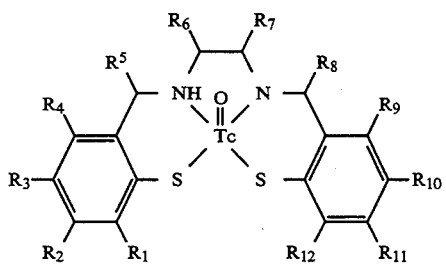

wherein $R_1$–$R_{12}$ are as defined above broadly and preferably.

A stannous salt such as stannous glucoheptonate or stannous chloride are preferred reducing agents. Specifically preferred are technetium-99m complexes of (1) N,N'-1,2-ethylenediylbis-L-cysteine, diethyl ester; (2) N,N'-1,2-ethylenediylbis-L-cysteine, dimethyl ester; and (3) N,N'-1,2-ethylenediylbis-L-cysteine, di-n-propyl ester.

DETAILED DESCRIPTION OF THE INVENTION

The diaminedithiol ligands of the present invention can be prepared by several methods of coupling appropriately substituted (and in some cases protected) amine, thiol, and aminethiol fragments. Preparation of the necessary fragments is possible by a wide variety of techniques known to one skilled in the art of organic synthesis. In the following reaction descriptions, $R_1$–$R_{12}$ are as described above except where stated to the contrary.

The diaminedithiol forming reactions include the reductive dimerization of substituted thiazolidines or a tetrahydro-1,3-thiazene of formula (III) to give the diaminedithiol acids of formula (IV). These can be esterified by reaction of a compound (IV) with an appropriate alcohol and catalyst to afford the ester substituted diaminedithiol of formula (V) (Scheme I). This general synthesis of ester-substituted diaminedithiols has been described by Blondeau et al. *Can. J, Chem.*, 45, 49 (1967).

Scheme I

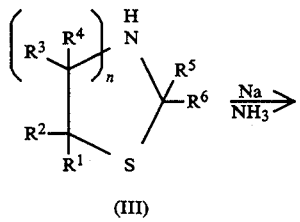

(III)

Scheme I -continued

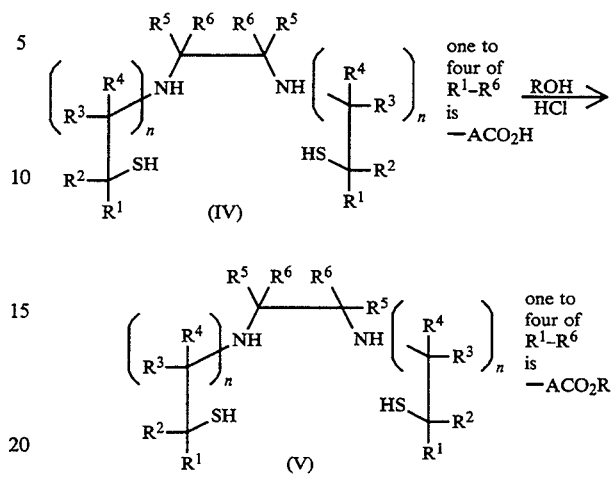

In particular, a thiazolidine or a tetrahydro-1,3-thiazene of formula (III) can be reacted with sodium in liquid ammonia, followed by esterification with methanol or ethanol using gaseous hydrogen chloride as catalyst to afford a compound of formula (V). Thiazolidines and tetrahydro-1,3-thiazenes of formula (III) are prepared by reaction of an amine-thiol with an aldehyde or ketone. (M. T. Nagasawa et al. *J. Med. Chem.*, 77. 591 (1984)).

Alternatively, a diaminedithiol can be prepared by the reductive amination of glyoxal or a 1,2-diketone or 1,3-diketone moiety of formula (VI) with an appropriately substituted (and protected) aminothiol of formula (VII) (Scheme II).

In particular, reaction of glyoxal or a ketone moiety with a protected ester aminethiol in the presence of a dehydrating agent Scheme II

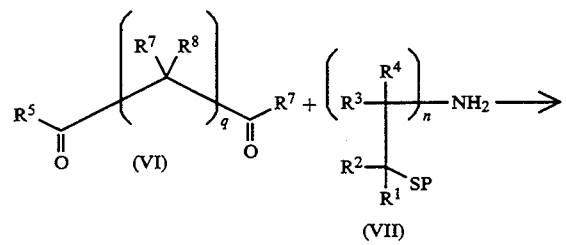

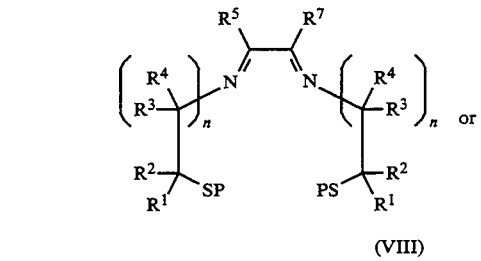

(VIII)

-continued

Scheme II

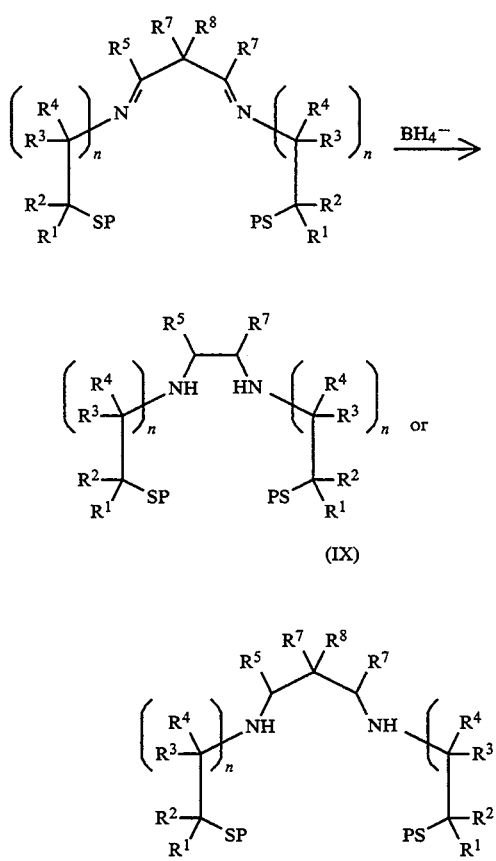

such as a molecular sieve, followed by reduction of the diimine intermediate of formula (VIII) with a borohydride reducing agent affords a protected diaminedithiol of formula (IX). Protecting group P, which can be any of a variety of protecting groups for sulfur, including methoxymethyl, methoxyethoxymethyl, p-methoxybenzyl or benzyl, can be removed by appropriate methods well known to one skilled in the art of organic synthesis such as trifluoroacetic acid, mercuric chloride, or sodium in liquid ammonia. In the case of Lewis acid labile groups including acetamidomethyl and benzamidomethyl, P can be left intact. Labeling of the ligand with technetium, in the case of Lewis acid labile protecting groups, will cleave the group P, rendering the protected diaminedithiol equivalent to the unprotected form.

For the preparation of unsymmetrical diaminedithiol ligands, a protected form of a compound of formula (VI), such as (X), can be used in a stepwise coupling sequence shown below (Scheme III).

Scheme III

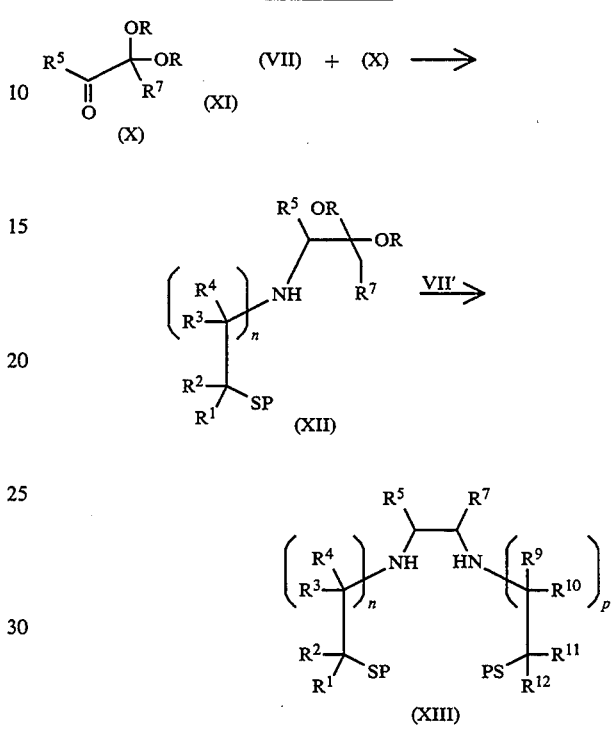

A protected aminethiol of formula (VII) is reductively aminated with a compound of formula (X) to afford the protected carbonyl compound of formula (XII). Deprotection, followed by reductive amination with a second aminethiol (VII') affords the unsymmetrical diaminedithiol ligand of formula (XIII), which may be deproteoted by an appropriate method, as described above. The reaction conditions are essentially the same as for the reductive amination of Scheme II starting with commercially available reagents or those prepared easily from commercially available reagents.

Aryl-containing diaminedithiols can be prepared by reaction of an appropriate amine with thiol-substituted benzaldehydes, as shown in Scheme IV to afford the diimines. These can then be reduced to the diamine with a reducing agent such as sodium borohydride. Alternatively, the aldehyde, amine and a cyanide nucleophile can be reacted in a Strecker synthesis to prepare the bis-amino-nitrile. Hydrolysis of this compound affords the bis-amino acid. Deprotection of the sulfur by appropriate methods as described previously is followed by esterification by methods described previously to afford the final compounds.

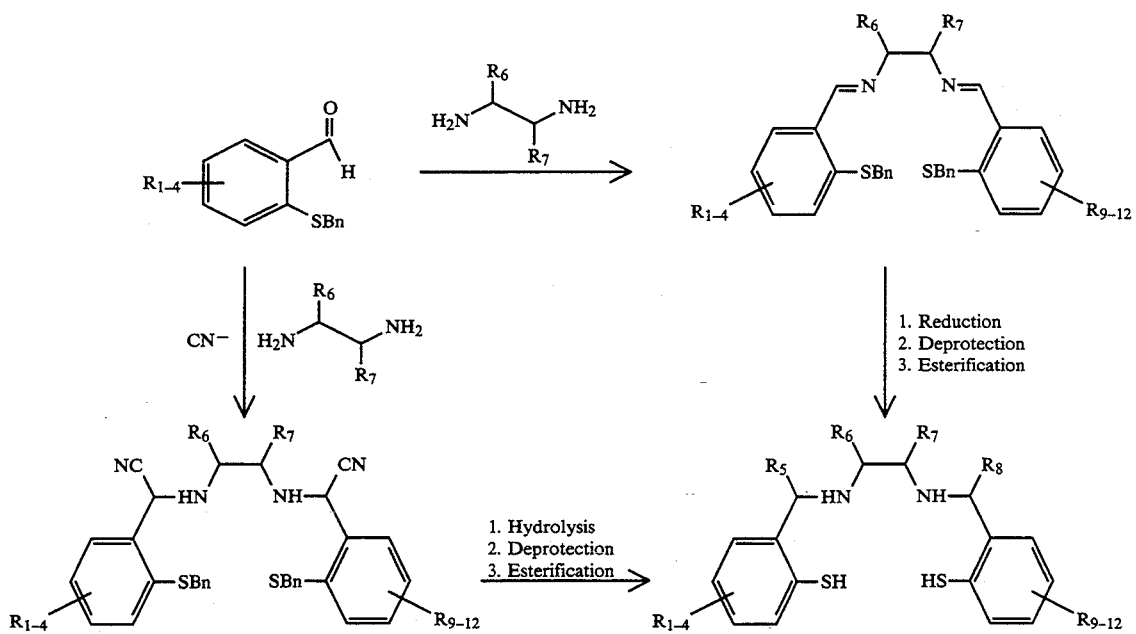

Particular diaminedithiol esters useful in the practice of this invention have the formulas:

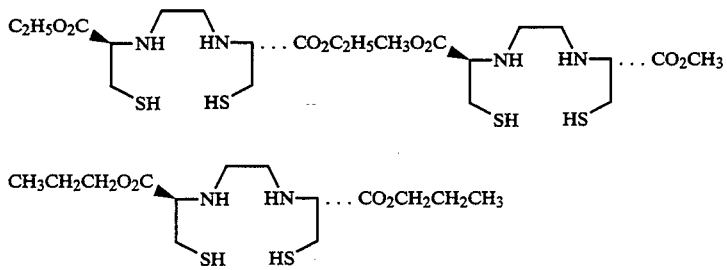

or pharmaceutically suitable salts thereof.

The invention can be further understood by the following examples in which parts and percentages are by weight unless otherwise indicated and temperatures are in degrees centigrade.

EXAMPLE 1

Synthesis of N,N'-1,2-ethylenediylbis-L-cysteine, diethyl ester, dihydrochloride Part A: Synthesis of (R)-thiazolidine-4-carboxylic acid, sodium salt To (R)-thiazolidine-4-carboxylic acid (45.0 g, 0.338 mol) in 600 mL absolute ethanol was added sodium hydroxide pellets (13.52 g, 0.338 mol). The slurry was stirred until the pellets were dissolved (30–45 min). The ethanol was removed under aspirator on a rotary evaporator, another 300 mL ethanol added and evaporated, and the remaining white solid placed under high vacuum overnight to remove residual traces of ethanol.

Part B: Synthesis of N,N'-1,2-ethylenediylbis-L-cysteine

A three-necked 1000 mL flask, equipped with a gas inlet, mechanical stirrer with glass paddle and dry ice condenser was cooled to $-78°$ and 450 mL ammonia condensed into the flask. The cooling bath was removed and the solution allowed to warm up for 30 min. Sodium spheres (3–8 mm, 14 g, 0.6 mol) were washed with pentane, soaked in 2-propanol for 10 min, and then washed twice more with pentane. The entire amount of thiazolidine sodium salt prepared in Part A above was added to the ammonia in one portion and fairly rapid stirring begun. The sodium spheres were added, 2–3 at a time, waiting 45–60 sec between additions, until a persistent blue color was obtained for 10 min. The addition took about 45 min and not all of the sodium was used. After 10 min of blue color, the reaction was quenched with solid ammonium chloride, the condenser removed, and the ammonia evaporated under nitrogen with the aid of a warm water bath. The white solid residue was dissolved in 400 mL of water and concentrated HCl added until the pH of the mixture was 2. The slurry was cooled to 0° for 1 h, then suction filtered through a medium porosity glass frit. The solids were washed with $2 \times 200$ mL water and dried over calcium sulfate in a dessicator under vacuum until a constant weight was obtained (18–24 h) to yield 31.8 g (70%) of a white powder, m.p. 230°–231° (decomposition, although darkening begins at 214°–216°). The material was insoluble in all solvents except aqueous base.

Part C: Synthesis of N,N'-1,2-ethylenediylbis-L-cysteine, diethyl ester, dihydrochloride N,N'-1,2-ethylenediylbis-L-cysteine from Part B (20.0 g 74.5 mmol) was slurried in 1200 mL absolute ethanol in a 2000 mL three-necked flask equipped with a gas inlet tube (a hollow tapered tube finishing in a 2 mm diameter bore) from an HCl tank, mechanical stirrer, and condenser with gas outlet hooked up to an HCl trapping system. Vigorous stirring was started and HCl gas bubbled in at a rate to maintain a rapid reflux of the ethanol. Gas addition was continued for 1.5 h, then reflux was continued for an additional 2.5 h. The slurry was then cooled to 0° for one hour in an ice bath, suction filtered (Whatman #1, Buchner funnel), and the solids washed with 2×100 mL cold ethanol to afford 26.4 g of crude diester (89%) after drying.

Part of this material was crystallized by slurrying the solids in 650 mL ethanol at 50° with stirring, and adding 80 mL water. The slightly cloudy solution was rapidly suction filtered (Whatman π1), stoppered, and allowed to crystallize in the refrigerator overnight. The material was filtered, washed with 2×100 mL cold ethanol, and dried under vacuum in a dessicator to Field 19.56 g (67%), m.p. 182° (decomposition with melting).

Part D: Purification of N,N'-1,2-ethylenediylbis-L-Cysteine, diethyl ester, dihydrochloride (This step was performed under GMP conditions, using approved solvents and reagents, and specially prepared glassware and equipment)

Sodium Carbonate (58.38 g, 0.55 mol) was dissolved in 1200 mL of deoxygenated sterile water with mechanical stirring under a nitrogen atmosphere. N,N'-1,2-ethylenediylbis-L-Cysteine, diethyl ester, dihydrochloride (175 g, 0.44 mol) was added to this solution, followed by diethyl ether (400 mL). The solution was stirred for 15 minutes, and the pH adjusted to 8.5-9.0 by the addition of more sodium carbonate, if necessary. The solution was poured into a separatory funnel and the layers separated. The aqueous portion was extracted with 4×200 mL of diethyl ether. The combined ether extracts were dried over sodium sulfate, filtered, and concentrated under reduced pressure on a rotary evaporator.

A solution of absolute ethanol (4300 mL), sterile water (520 mL), and conc. hydrochloric acid (103 g) was heated, with stirring, to 70°. The concentrated residue was added to this solution, and the flask which contained the residue was rinsed out with 2×300 mL ethanol, which was then also added to the hot solution. Heating was continued until the solution was clear, at which time it was rapidly suction filtered through a glass fiber filter (Whatman GF/D). The flask which contained the solution was rinsed with 2×300 mL ethanol, which was also passed through the filter. The filtered solution was stoppered and stored at 0° for 24 hours. The resulting crystalline material was suction filtered (Whatman #1), washed twice with ethanol, twice with diethyl ether, and dried under vacuum to obtain a highly purified, pharmaceutically acceptable form of N,N'-1,2-ethylenediylbis-L-Cysteine, diethyl ester, dihydrochloride. Yield is 140 g (80%), m.p. 182-185° (decomposition).

EXAMPLE 2

Synthesis of N,N'-1,2-ethylenediylbis-L-cysteine, dimethyl ester, dihydrochloride N,N'-ethylenediylbis-L-cysteine prepared as in Example 1, Part B (15.0 g, 0.56 m) was slurried in 500 mL of methanol and hydrogen chloride gas was bubbled in at a vigorous rate to maintain the methanol at reflux and to dissolve the solids. After one hour of gas addition, the solution was refluxed an additional two hours. Cooling on ice for one hour resulted in crystallization. Filtration and drying afforded 9.4 g (47%) of the dimethylester dihydrochloride, m.p. 188°. Purification of this material can be accomplished as described in Example 1. Part D.

EXAMPLE 3

Synthesis of N,N'-1,2-ethylenediylbis-D-(S-benzamidomethyl)-penicillamine, dimethyl ester, dihydrochloride Part A: Synthesis of S-benzamidomethyl-(S)-penicillamine methyl ester (S)-Penicillamine methyl ester hydrochloride (1.0 g, 5.0 mmol) was dissolved in neat trifluoroacetic acid (5 mL) under nitrogen. Benzamidomethanol (0.76 g. 5.0 mmol) was added and the solution stirred for one hour at 25°. The solvent was evaporated on a rotary evaporator to give the desired product as a crystalline trifluoroacetate salt. This was not further purified, but converted directly into the free base. The solid was dissolved in water (10 mL) and saturated sodium bicarbonate solution added until gas evolution ceased and pH>8.5. The aqueous solution was extracted with ethyl acetate (2×15 mL), the extracts dried over sodium sulfate. filtered, and evaporated to yield 0.62 g (42%) of the product as a clear oil.

Part B: Synthesis of N,N'-1,2-ethylenediylbis-D-(S-benzamidomethylpenicillamine), dimethyl ester, dihydrochloride S-benzamidomethyl-(S)-penicillamine methyl ester (0.3 g 1.0 mmol) was placed in a flask with 3 mL of ethanol under nitrogen. Molecular sieves (10–12, 3A) were placed in the flask and glyoxal (40% aqueous solution, 73 mg, 0.5 mmol) was added. The reaction was stirred overnight at room temperature and then three hours at 40°, at which time the resulting slurry was filtered and sodium cyanoborohydride (1.29 g, 2.05 mmol) added to the filtrate. After stirring for 4 h at room temperature, the solvent was evaporated and the residue dissolved in water (20 mL) and extracted with ethyl acetate (3×15 mL). This resulting solution was dried over sodium sulfate, filtered, and evaporated. The residue was purified by flash chromatography (70:30 ethyl acetate:hexane) and the appropriate fractions (determined by TLC) were evaporated. Treatment with ethanolic hydrogen chloride until pH<1 followed by evaporation yielded 80 mg (23%) of the product as a white solid. m.p. 142°-145°.

Using the synthesis procedures described above. the diaminedithiols of Examples 1-3 and other diaminedithiol compounds which can be prepared are shown in Table 1.

TABLE 1

Structure: R³-C(R⁴)(NH-)-C(R⁵)(R⁶)-... with R¹,R² on C bearing SP; R⁷,R⁸ on C; R⁹,R¹⁰ on C; R¹¹,R¹² on C bearing PS.

| Ex. No. | Stereo-Chem. | m.p. °C | R¹ | R² | R³ | R⁴ | R⁵ | R⁶ | R⁷ | R⁸ | R⁹ | R¹⁰ | R¹¹ | R¹² | P |
|---|---|---|---|---|---|---|---|---|---|---|---|---|---|---|---|
| 1 | L,L | 182 | H | H | $CO_2C_2H_5$ | H | H | H | H | H | H | $CO_2C_2H_5$ | H | H | H |
| 2 | L,L | 188 | H | H | $CO_2CH_3$ | H | H | H | H | H | H | $CO_2CH_3$ | H | H | H |
| 3 | D,D | 142–145 | $CH_3$ | $CH_3$ | $CO_2CH_3$ | H | H | H | H | H | H | $CO_2CH_3$ | $CH_3$ | $CH_3$ | BZM* |
| 4 | D,D | 115–119 | $CH_3$ | $CH_3$ | $CO_2C_2H_5$ | H | H | H | H | H | H | $CO_2C_2H_5$ | $CH_3$ | $CH_3$ | BZM* |
| 5 | L,L | 160–164 | H | H | $CO_2C_3H_7$ | H | H | H | H | H | H | $CO_2C_3H_7$ | H | H | H |
| 6 | L,L |  | H | H | $CO_2C_4H_9$ | H | H | H | H | H | H | $CO_2C_4H_9$ | H | H | H |
| 7 | D,D | 182–185 | H | H | $CO_2C_2H_5$ | H | H | H | H | H | H | $CO_2C_2H_5$ | H | H | H |
| 8 | L,L |  | H | H | $CO_2C_2H_5$ | H | $CH_3$ | H | $CH_3$ | H | H | $CO_2C_2H_5$ | H | H | BZM* |
| 9 | mix | 104–105 | H | H | $CO_2C_2H_5$ | H | $CO_2C_2H_5$ | H | $CO_2C_2H_5$ | H | H | $CO_2C_2H_5$ | H | H | H |
| 10 | mix | 145–146 | H | H | H | H | $CO_2C_2H_5$ | H | $CO_2C_2H_5$ | H | H | H | H | H | H |
| 11 | mix |  | $CH_3$ | $CH_3$ | H | H | H | H | H | H | H | H | $CH_3$ | $CH_3$ | BZM |
| 12 | L,L |  | H | H | $CH_2CO_2C_2H_5$ | H | H | H | H | H | H | $CH_2CO_2C_2H_5$ | H | H | H |
| 13 | mix |  | H | H | $(CH_2)_3CO_2C_2H_5$ | H | H | H | H | H | H | $(CH_2)_3CO_2C_2H_5$ | H | H | BZM |
| 14 | mix |  | $C_6H_{13}$ | $C_6H_{13}$ | $CO_2CH_3$ | H | H | H | H | H | H | $CO_2CH_3$ | $C_6H_{13}$ | $C_6H_{13}$ | H |
| 15 | L,L |  | H | H | $CO_2C_2H_5$ | H | H | H | H | H | H | H | H | H | BZM |
| 16 | L,L |  | H | H | $CO_2C_2H_5$ | H | H | H | $CH_3$ | $CH_3$ | H | $CO_2C_2H_5$ | H | H | H |
| 17 | mix |  | $CO_2C_2H_5$ | H | H | H | H | H | H | H | H | H | H | $CO_2C_2H_5$ | BZM |
| 18 | L,L |  | H | H | $CO_2C_2H_5$ | $(CH_2)_6CO_2CH_3$ | H | H | H | H | $(CH_2)_6CO_2CH_3$ | H | H | H | H |
| 19 | L,L |  | $CH_3$ | $CH_3$ | $CO_2C_2H_5$ | H | H | H | H | H | $CO_2C_2H_5$ | H | $CH_3$ | $CH_3$ | H |
| 20 | L,L |  | H | H | $CO_2iC_3H_7$ | H | H | H | H | H | $CO_2iC_3H_7$ | H | H | H | H |
| 21 | L,L |  | H | H | $CO_2CH_2C(CH_3)_3$ | H | H | H | H | H | $CO_2CH_2C(CH_3)_3$ | H | H | H | H |
| 22 | L,L |  | H | H | $CO_2CH_2CH(CH_3)_2$ | H | H | H | H | H | $CO_2CH_2CH(CH_3)_2$ | H | H | H | H |
| 23 | L,L |  | H | H | $CO_2(CH_2)_4CH_3$ | H | H | H | H | H | $CO_2(CH_2)_4CH_3$ | H | H | H | H |
| 24 | L,L |  | H | H | H | $CO_2CH_3$ | $(CH_2)_9CH_3$ | H | H | H | H | $CO_2CH_3$ | H | H | BZM* |
| 25 | L,L |  | H | H | H | $(CH_2)_9CO_2CH_3$ | H | H | H | H | H | $(CH_2)_9CO_2CH_3$ | H | H | BZM* |
| 26 | mix |  | H | H | H | H | H | $CO_2(CH_2)_9CH_3$ | H | H | H | H | H | H | H |
| 27 | L,L |  | H | H | H | $CO_2CH_2C_6H_5$ | H | H | H | H | H | $CO_2CH_2C_6H_5$ | H | H | BZM* |
| 28 | L,L |  | H | H | H | $CO_2(p-NO_2C_6H_5)$ | H | H | H | H | H | $CO_2(p-NO_2C_6H_5)$ | H | H | H |
| 29 | L,L |  | H | H | H | $CO_2C_6H_5$ | H | H | H | H | H | $CO_2C_6H_5$ | H | H | H |
| 30 | mix |  | H | H | H | H | H | $CO_2(4-C_5H_4N)$ | H | H | H | H | H | H | BZM* |
| 31 | L,L |  | H | H | H | $CO_2(3,4,5-C_6H_2F_3)$ | H | H | H | H | H | $CO_2(3,4,5-C_6H_2F_3)$ | H | H | H |

BZM = Benzamidomethyl
Using the synthesis procedure set forth in Scheme IV, other diaminedithiols which can be prepared are shown in Table 2.

TABLE 2

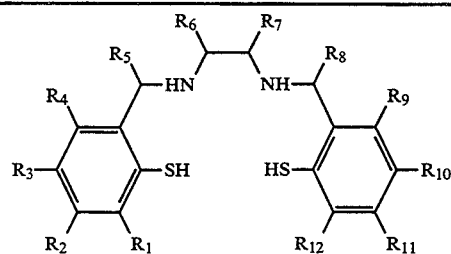

| Ex No. | Stereo Chem. | $R^1$ | $R^2$ | $R^3$ | $R^4$ | $R^5$ | $R^6$ |
|---|---|---|---|---|---|---|---|
| 32 | mix | H | H | H | H | $CO_2CH_3$ | H |
| 33 | — | $CO_2C_2H_5$ | H | H | H | H | H |
| 34 | — | H | $CH_2CO_2CH_3$ | H | H | H | $(CH_2)_3CH_3$ |
| 35 | — | H | H | $CO_2CH_2C_6H_5$ | H | H | H |
| 36 | — | H | H | H | $(CH_2)_6CO_2CH_3$ | H | H |
| 37 | mix | H | H | $CO_2CH_3$ | H | $CO_2CH_3$ | H |
| 38 | mix | H | H | $(CH_2)_2CH_3$ | H | H | $CO_2CH_3$ |
| 39 | mix | H | H | H | H | H | $CO_2CH_3$ |
| 40 | — | H | H | $(CH_2)_{10}CO_2CH_3$ | H | H | H |
| 41 | mix | H | H | H | H | $CO_2C_6H_5$ | H |
| 42 | mix | H | H | H | H | $CO_2(p-NO_2C_6H_5)$ | H |
| 43 | mix | $CH_3$ | H | $CH_3$ | H | $CO_2(4-C_5H_4N)$ | H |
| 44 | mix | H | H | H | H | H | $CO_2(CH_2)_9CH_3$ |

| Ex No. | $R^7$ | $R^8$ | $R^9$ | $R^{10}$ | $R^{11}$ | $R^{12}$ |
|---|---|---|---|---|---|---|
| 32 | H | $CO_2CH_3$ | H | H | H | H |
| 33 | H | H | H | H | H | $CO_2C_2H_5$ |
| 34 | $(CH_2)_3CH_3$ | H | H | H | $CH_2CO_2CH_3$ | H |
| 35 | H | H | H | $CO_2CH_2C_6H_5$ | H | H |
| 36 | H | H | $(CH_2)_6CO_2CH_3$ | H | H | H |
| 37 | H | $CO_2CH_3$ | H | $CO_2CH_3$ | H | H |
| 38 | H | H | H | $(CH_2)_2CH_3$ | H | H |
| 39 | $CO_2CH_3$ | H | H | H | H | H |
| 40 | H | H | H | $(CH_2)_{10}CO_2CH_3$ | H | H |
| 41 | H | $CO_2C_6H_5$ | H | H | H | H |
| 42 | H | $CO_2(p-NO_2C_6H_5)$ | H | H | H | H |
| 43 | H | $CO_2(4-C_5H_4N)$ | H | $CH_3$ | H | $CH_3$ |
| 44 | H | H | H | H | H | H |

The radiopharmaceutical complexes of the present invention can easily be prepared by admixing a salt of a radioactive metal and the diaminedithiol ligand in the presence of a suitable reducing agent, if required, in aqueous media at temperatures from room temperature to reflux temperature or even higher, and are obtained and isolatable in high yield at both macro (carrier added. e.g., $^{99}Tc$) concentrations and at tracer (no carrier added. e.g., $^{99m}Tc$) concentrations of less than $10^{-6}$ molar. In some cases the diaminedithiol ligand may itself act as the reducing agent thus eliminating the need for an additional reducing agent. Suitable additional reducing agents, when required or desired are well known to those skilled in the art. The reaction is generally complete after 1 minute to 2 hours, depending upon the identity of the particular reagents employed. The radiolabelled complex is made in the same way as any corresponding non-radioactive diaminedithiol complex by simply substituting the desired radionuclide for the corresponding non-radioactive element in the starting materials, except in the case of technetium because all technetium isotopes are radioactive.

In the case of technetium such as, for example $^{99}Tc$ or $^{99m}Tc$, a complex in accord with this invention is preferably made by mixing pertechnetate ($Tc^{+7}$) with the desired diaminedithiol in aqueous medium, then adding to the reaction mixture an appropriate reducing agent capable of reducing the technetium. Among suitable reducing agents are alkali metal dithionites, stannous salts, sodium borohydride, and others, as is well known.

The diaminedithiol technetium complexes of this invention can also be prepared from preformed technetium complexes by treating these preformed complexes with an excess of ligands under suitable conditions. For example, the technetiumdiaminedithiol complex can also be prepared by reacting the desired diaminedithiol ligand with the tetrahalo-oxo complex of $Tc^{+5}$ or with a technetium-glucoheptonate complex, or the like.

An excess of the diaminedithiol ligand, up to 50 to 100 fold molar excess or more, and an excess of reducing agent, can be used in the complexing reaction to ensure maximum yield from the technetium. Following the reaction, the desired complex can be separated from the reaction mixture, if required, by crystallization or precipitation or by conventional chromatography.

Kits in accord with the present invention comprise a sterile, non-pyrogenic, diaminedithiol ligand and, if required, a quantity of a reducing agent for reducing a preselected radionuclide. Preferably, such kits contain a predetermined quantity of a sterile diaminedithiol ligand and a predetermined quantity of a sterile reducing agent capable of reducing a predetermined quantity of the preselected radionuclide. It is also preferred that the diaminedithiol ligand and reducing agent be lyophilized, when possible, to facilitate storage stability. If lyophilization is not practical, the kits can be stored frozen or in solution at room temperature. The choice of radionuclides will in general be dependent on the final use of the labeled product. Of course, because of the availability of technetium-99m generators, such a radionuclide is especially preferred.

In one embodiment of the invention, a kit for use in making the complexes of the present invention from a supply of $^{99m}$Tc such as the pertechnetate solution in isotonic saline available in most clinical laboratories includes the desired quantity of a selected ligand to react with a selected quantity of pertechnetate, and a reducing agent such as stannous chloride in an amount sufficient to reduce the selected quantity of pertechnetate to form the desired complex.

A preferred kit for the facile preparation of the desired Tc-99m radiopharmaceutical, in accordance with the present invention, is comprised of two vials. One vial (A) contains the ester derivatized diaminedithiol ligand prepared in lyophilized form at acidic pH, where ligand stability is optimal, and an inert filler, such as mannitol, to provide easy lyophilization. The second vial (B) contains a reductant suitable to convert the $^{99m}$Tc to the desired oxidation state and an inert filler such as mannitol. The second vial is lyophilized at a pH of approximately 9. When the contents of the vials are mixed together with sterile saline, an optimal pH ~3.0–5.0 is obtained. This provides optimal reaction of the diaminedithiol ligand with the reduced $^{99m}$Tc to prepare the desired radiopharmaceutical in high yield and high purity. One method by which the Tc-99m radiopharmaceutical can be prepared in high yield is as follows:

One vial (A) is prepared as a sterile, non-pyrogenic, freeze-dried material containing the dihydrochloride salt of the ester-derivatized diaminedithiol ligand at levels of 100 μg to 2 mg, or higher, with a suitable inert filler such as mannitol, to provide a suitable plug after freeze-drying.

The second vial (B) is prepared as a sterile, non-pyrogenic, freeze-dried material containing a suitable reductant, such as a stannous salt (e.g., SnCl$_2$), at levels of 5 μg to 100 μg, or more. Vial B may also contain a ligand to stabilize Sn(II), such as ethylene diamine tetraacetic acid (EDTA) at a level of 100 μg to 1.0 mg, or more. In addition, a bulking agent such as mannitol may be used to aid in lyophilization.

The $^{99m}$Tc radiopharmaceutical, as described in the present invention, is prepared by admixing the contents of vials (A) and (B) with $^{99m}$TcO$_4$ from a $^{99}$Mo/$^{99m}$Tc radiopharmaceutical generator using sterile techniques well known to those skilled in the art of preparing sterile injectable materials. The generator eluant added should provide about 20–50 mCi of activity. After 15 minutes at room temperature, the $^{99m}$Tc diaminedithiol complex, as described herein, is formed in high radiochemical yield (e.g., >80%).

The following examples illustrate the preparation of technetium-99m complexes of the present invention.

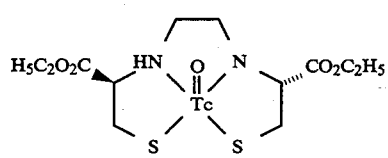

Example A

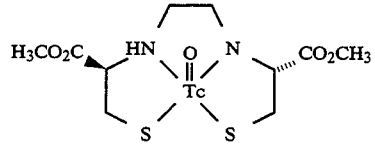

Example B

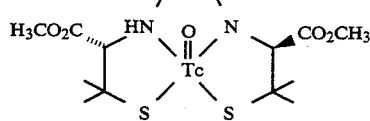

Example C

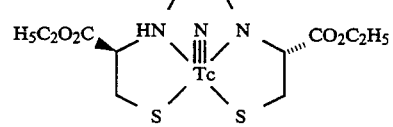

Example D

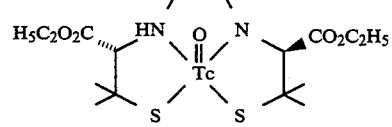

Example E

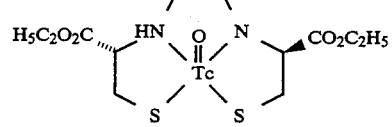

Example F

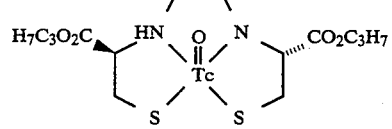

Example G

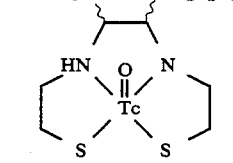

Example H

These technetium-99m complexes were prepared using standard labeling conditions similar to those reported in the literature for other diaminedithiol ligands. For all of the complexes except the complex of Example D, a Glucoscan TM kit (a mixture of sodium glucoheptonate and stannous chloride) was reconstituted with 50–150 mCi of $^{99m}$TcO$_4^-$ obtained by elution of a $^{99}$Mo/$^{99m}$Tc radionuclide generator. The diaminedithiol (1–10 mg) in water (0.2–1.0 mL) was added and the mixture allowed to stand for 1 to 30 minutes. In the case of the complexes of Examples C, E and I, warming was necessary to effect removal of the benzamidomethyl protecting groups. For the complex of Example D, a modification of the procedure of Baldas et al., Int. J. Appl. Radiat. Isot., 36, 133 (1985) was used. Generator eluate (100–200 mCi) was reduced to dryness by rotary evaporation and 15 mL 12M HCl followed by 15 mg sodium azide were added with stirring. After standing for 5 minutes, the mixture was reduced to dryness by rotary evaporation and redissolved in 1 mL buffer (0.05M sodium phosphate, pH 7.0). The diaminedithiol (1-10 mg) in 0.2-2 mL saline was added to the residue from above and the mixture was allowed to stand at room temperature for 1 to 30 minutes, warming if necessary to complete the reaction.

Once the complexes were prepared, they were purified by high pressure liquid chromatography on a Brownlee RP-8 Spheri 5 column using a 0.05M ammonium acetate (NH$_4$OAc)/methanol gradient. The gradient typically ran from 20-40% methanol initially up to 100% methanol over 15 minutes and included an initial hold period at the start of the gradient of 1-10 minutes, and the purified complexes were isolated by rotary evaporation of the solvent at room temperature. The complexes obtained in this fashion were evaluated for purity by thin layer chromatography on Whatman C-18 reversed-phase plates using a solvent mixture containing 65% methanol, 5% tetrahydrofuran, 10% acetonitrile, and 20% 0.5M NH$_4$OAc. In all cases, radiochemical purity was greater than 90%. Solutions of the complexes in saline were shown to be stable for at least 4 hours.

The complexes are injected intravenously, usually in saline solution, at a dose of 5 to 100, preferably 5 to 50 millicuries per 70 kg of body weight and imaging is conducted by known procedures.

UTILITY

The above-described complexes were evaluated for potential clinical utility as radiopharmaceuticals for the evaluation of regional cerebral blood flow by performing brain imaging studies in rhesus monkeys. From these studies, brain extraction (% injected dose), and brain retention (T ½) were determined.

METHODS

Male rhesus monkeys were food deprived for 24 hours prior to induction of anesthesia with an intramuscular injection of a mixture of Ketamine hydrochloride (10 mg/kg) and Acepromazine maleate (1 mg/kg). Subsequent injections of sodium pentobarbitol (65 mg/mL) via an external saphenous vein catheter were given to maintain anesthesia. Immediately prior to imaging 18-22 mCi of the technetium-99m complex were administered via the saphenous vein catheter.

Dynamic planar imaging was performed using a Picker Digital Dyna Camera (Picker Int., Northford. Conn.) interfaced to a Computer Design and Applications (CDA) Microdelta nuclear medicine computer (CDA, Waltham. Mass.). The animal to be imaged was secured on a patient pallet with its head in the left lateral position in the center of the camera's field of view. Data was acquired dynamically into a 64×64 word mode matrix, one frame per minute for up to two hours, using a zoom mode of 2×.

Time-activity curves were acquired using a region of interest (ROI) that enclosed the brain as defined by an isocontour marking a count density change of between 25 and 45 percent of the maximum. A background ROI was placed just outside the occipital area of the brain and followed the contour of the brain ROI. The number of counts per pixel in each ROI per mCi injected was calculated for each of the one minute images in the experiment. The counts in both ROIs are decay corrected and the background counts subtracted from the brain ROI counts.

The percent injected dose (% I.D.) was calculated using the results of the time-activity curves. The peak counts per pixel per mCi were converted to peak disintegrations per minutes. The number of disintegrations in the brain were converted to mCi in the brain and compared to the injected dose, giving a % I.D. in the brain.

The retention time of the complex in the brain is described by the half-life (t ½). Half-life calculations were performed using a commercially available exponential stripping package and a non-linear pharmacokinetic modeling program (Statistical Consultants. Inc. (1986) "PCNONLIN and NONLIN: Software for the Statistical Analysis of Nonlinear Models" *The American Statistician.* Vol. 40, 52). Initial estimates of washout rates were determined using the exponential stripping package. These estimates were used in the PCNONLIN modeling program for the determination of washout kinetics and biological T ½. It was assumed that the complexes followed one compartment kinetics. If the data did not support this assumption, then multicompartmental analysis was applied.

The results are shown in Table II.

TABLE II

CHEMICAL AND BIOLOGICAL CHARACTERISTICS PARTITION COEFFICIENT, BRAIN EXTRACTION AND RETENTION OF $^{99m}$Tc COMPLEXES

| EX. NO. | PARTITION COEFFICIENT[1] | MONKEY IMAGING | |
|---|---|---|---|
| | | % I.D.[2] | T 1/2 min[3] |
| A | 44 | 4.8 ± .8 (6) | >1440 (6) |
| B | 7 | 2.9 ± 2.4 (5) | 167 ± 15 (3) |
| C | 35 | 3.0 (1) | <30 (1) |
| D | 12 | 2.8 ± 0.2 (2) | >1440 (2) |
| E | 142 | 3.2 (1) | <30 |
| F | 52 | 3.2 (2) | <30 |
| G | 310 | 4.6 ± 0.6 (3) | >1440 |
| H | 19 | <2 (1) | <30 |

All values are Mean ± SEM
Value in parenthesis is the number of animals used in the calculation.
[1]Octanol/water partition coefficient.
[2]Maximum % I.D. as determined by planar imaging.
[3]Estimated half-life of brain clearance.

Another important criteria for a radio-pharmaceutical for the evaluation of regional cerebral blood flow is that the radiopharmaceutical be distributed as a function of blood flow. Distribution as a function of blood flow can be demonstrated from analysis of SPECT images.

Formatted SPECT images were analyzed using a densitometric video based camera system (Loats ® Assoc., Westminster, Md.) in order to obtain information about the concentration and distribution pattern of $^{99m}$Tc. Radioactivity in various brain areas were assumed to be positively and linearily related to changes in film absorbance. Brain area mean absorbance per pixel value was calculated. Neuroanatomical landmarks for placement of brain area ROI were based on human brain positron emission tomography atlases. Ratios of absorbance between different gray matter areas (cortical areas and thalamus) and a white matter reference area were determined at about 50 and 150 minutes post-administration.

This analysis was performed using the complex of Example A. The results are summarized in Table III, and show that a gray/white ratio of 2-3:1 is observed for the complex of Example A, consistent with distribution as a function of cerebral blood flow.

TABLE III

MONKEY BRAIN AREA ACTIVITY RATIOS DERIVED FROM FORMATED SPECT IMAGES OF THE COMPLEX OF EXAMPLE A

| Regions | Time Post Compound Administration (min) | |
|---|---|---|
|  | 53 | 150 |
| Occipital Cortex | 3.3 | 2.6 |
| Parietal Cortex | 3.1 | 2.5 |
| Frontal Cortex | 2.9 | 2.3 |
| Thalamus | 2.5 | 2.1 |

Values are percent absorbance ratio for regions of interest to the corpus callosum-lateral ventrical (i.e. white matter reference area).

The diaminedithiol radiolabelled complexes, particularly those labelled with Tc-99m, are also useful in labeling white blood cells in vitro.

While the diaminedithiol complexes specifically described herein are particularly beneficial in radioimaging brain perfusion in mammals, aminated (N-containing) groups and other groups described in the art. and other unspecified materials and conditions are not excluded so long as they do not prevent the benefits of the invention from being realized.

What is claimed is:

1. An ester-substituted diaminedithiol of the formula:

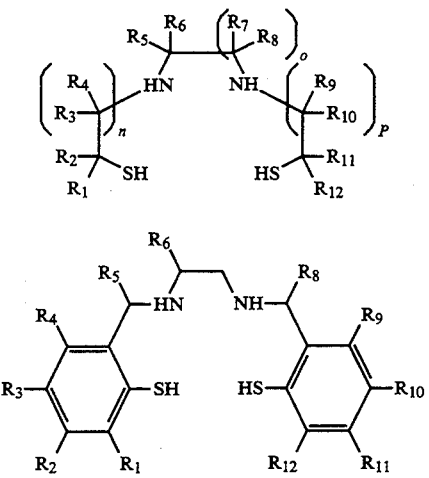

or a pharmaceutically suitable salt thereof wherein:
each of $R_1$–$R_{12}$ individually is selected from the group consisting of H, alkyl of 1–10 carbon atoms and —A—COOR wherein A is a straight or branched chain alkylene of 0–10 carbon atoms, n, o, and p are independently 1 or 2, and R is (a) alkyl of 1–10 carbon atoms, (b) phenyl or benzyl optionally substituted with up to 5 ring substituents each selected from alkyl of 1–4 carbon atoms, fluoro, chloro, bromo, nitro, alkoxy of 1–4 carbon atoms, carboxyl, or a carboxylic acid ester of 1–4 carbon atoms,
said ester-substituted diaminedithiol in sterile, pharmaceutically acceptable form.

2. An ester-substituted diaminedithiol of the formula:

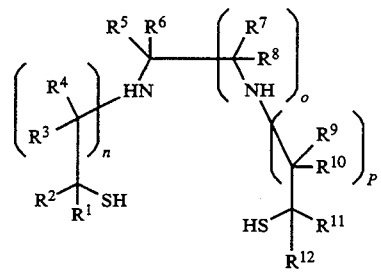

or a pharmaceutically suitable salt thereof wherein:
each of $R^1$–$R^{12}$ individually is selected from the group consisting of H, alkyl of 1–10 carbon atoms and —A—COOR wherein A is a straight or branched chain alkylene of 1–10 carbon atoms, n, o, and p are independently 1 or 2, and R is (a) alkyl of 1–10 carbon atoms, with the proviso that at least on of $R^1$–$R^{12}$ is —A—COOR,
said ester-substituted diaminedithiol in sterile, pharmaceutically acceptable form.

3. A diaminedithiol of claim 2 wherein R and any alkyl in $R^1$–$R^{12}$ is from 1–3 carbon atoms.

4. A diaminedithiol of claim 2 wherein A is a straight chain alkylene of 0–3 carbon atoms.

5. A diaminedithiol of claim 2 wherein $R^3$ and $R^{10}$ are —A—COOR and $R^4$ and $R^9$ are H.

6. A diaminedithiol of claim 2 wherein A is a bond and R is ethyl.

7. A diaminedithiol of claim 2 wherein n, o and p are 1, $R^3$ and $R^{10}$ are —A—COOR where A is a straight chain alkylene of 0–3 carbon atoms and R is alkyl of 1–3 carbon atoms, $R^4$ and $R^9$ are H, and $R^1$, $R^2$, $R^5$, $R^6$, $R^7$, $R^8$, $R^{11}$ and $R^{12}$ individually are selected from the group consisting of H, and alkyl of 1–3 carbon atoms.

8. A diaminedithiol of claim 2 wherein 1–4 of $R^1$–$R^{12}$ is —A—COOR.

9. A diaminedithiol of claim 2 wherein A is a bond and the stereochemistry at the position where that bond is attached to the diaminedithiol backbone is L.

10. The sterile, pharmaceutically acceptable diaminedithiol of claim 2 which is N,N'-1,2-ethylenediylbis-L-cysteine diethylester, dihydrochloride.

11. The sterile, pharmaceutically acceptable diaminedithiol of claim 2 which is N,N'-1,2-ethylenediylbis-L-cysteine, dimethylester, dihydrochloride.

12. The sterile pharmaceutically acceptable diaminedithiol of claim 2 which is N,N'-1,2-ethylenediylbis-L-cysteine, di-n-propylester, dihydrochloride.

13. A kit comprising a predetermined quantity of a sterile, pharmaceutically acceptable ester-substituted diaminedithiol of claim 1 and a predetermined quantity of a sterile, non-pyrogenic reducing agent for reducing a preselected radionuclide.

14. A kit comprising a predetermined quantity of a sterile, pharmaceutically acceptable ester-substituted diaminedithol of claim 2 and a predetermined quantity of a sterile, non-pyrogenic reducing agent for reducing a preselected radionuclide.

15. A kit of claim 14 wherein the reducing agent is a stannous salt for reducing technetium-99m.

16. A kit of claim 15 wherein the diaminedithiol is a diaminedithiol of claim 3.

17. A kit of claim 15 wherein the diaminedithiol is a diaminedithiol of claim 4.

18. A kit of claim 15 wherein the diaminedithiol is a diaminedithiol of claim 5.

19. A kit of claim 15 wherein the diaminedithiol is a diaminedithiol of claim 6.

20. A kit of claim 15 wherein the diaminedithiol is a diaminedithiol of claim 7.

21. A kit of claim 15 wherein the diaminedithiol is a diaminedithiol of claim 8.

22. A kit of claim 15 wherein the diaminedithiol is the diaminedithiol of claim 9.

23. A kit of claim 15 wherein the diaminedithiol is the diaminedithiol of claim 10.

24. A kit of claim 15 wherein the diaminedithiol is the diaminedithiol of claim 11.

25. A kit of claim 15 wherein the diaminedithiol is the diaminedithol of claim 12.

* * * * *

UNITED STATES PATENT AND TRADEMARK OFFICE
CERTIFICATE OF CORRECTION

PATENT NO. : 5,431,900

DATED : JULY 11, 1995

INVENTOR(S): PAUL LOUIS BERGSTEIN, EDWARD HOLLISTER CHEESMAN and ALAN DAVID WATSON It is certified that errors appear in the above-identified patent and that said Letters Patent is hereby corrected as shown below:

At column 4, line 33, for the structure under Formula (II), the "O" at line 33 should be deleted and --N-- inserted therefor.

At column 8, line 11, under Scheme III, the roman numerals in parenthesis "(XI)" should be deleted.

At column 9, line 1, the diagram should be titled by inserting --Scheme IV--.

At column 9, line 30 through 34, the diaminedithiol esters should appear as follows:

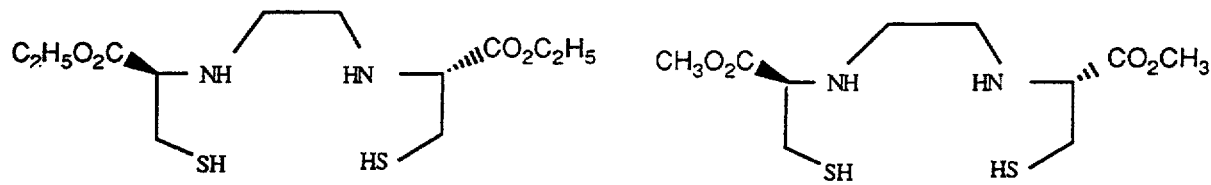

UNITED STATES PATENT AND TRADEMARK OFFICE
CERTIFICATE OF CORRECTION

PATENT NO. : 5,431,900

DATED : JULY 11, 1995

INVENTOR(S): PAUL LOUIS BERGSTEIN, EDWARD HOLLISTER CHEESMAN and ALAN DAVID WATSON It is certified that errors appear in the above-identified patent and that said Letters Patent is hereby corrected as shown below:

At column 16, line 46, delete "technetiumdiaminedithiol" and insert --technetium-diaminedithiol--.

At column 18, the structure under Example D should be deleted and the following structure added therefor:

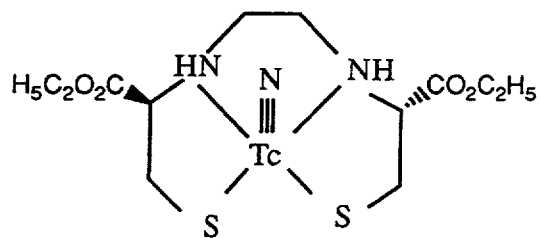

UNITED STATES PATENT AND TRADEMARK OFFICE
CERTIFICATE OF CORRECTION

PATENT NO. : 5,431,900
DATED : July 11, 1995
INVENTOR(S) : Paul Louis Bergstein, et al.

It is certified that error appears in the above-indentified patent and that said Letters Patent is hereby corrected as shown below:

At column 21, line 41, the ester-substituted diaminedithiol formula B should be deleted and the following structure added therefor:

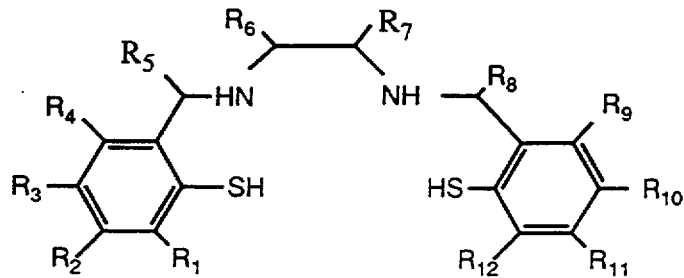

Signed and Sealed this

Tenth Day of September, 1996

Attest:

BRUCE LEHMAN

Attesting Officer    Commissioner of Patents and Trademarks